United States Patent [19]

Diamond et al.

[11] 4,215,218

[45] Jul. 29, 1980

[54] DIRECT REACTION OF ANILINES WITH OLEFINS

[75] Inventors: Steven E. Diamond, Randolph; Frank Mares, Whippany, both of N.J.

[73] Assignee: Allied Chemical Corporation, Morris Township, Morris County, N.J.

[21] Appl. No.: 834,640

[22] Filed: Sep. 19, 1977

[51] Int. Cl.$^2$ .................. C07D 215/06; C07C 87/62
[52] U.S. Cl. .................................. 546/162; 260/577
[58] Field of Search .................. 260/577, 283 SY; 546/162

[56] References Cited

U.S. PATENT DOCUMENTS

| | | | |
|---|---|---|---|
| 2,608,557 | 8/1952 | Copenhaver | 260/283 SY |
| 2,984,687 | 5/1961 | Esmay et al. | 260/577 |
| 3,705,163 | 12/1972 | Horvitz et al. | 260/283 SY |
| 3,758,586 | 9/1973 | Coulson | 260/577 |

FOREIGN PATENT DOCUMENTS 566540 11/1958 Canada ........................ 260/577

*Primary Examiner*—Donald G. Daus
*Assistant Examiner*—D. B. Springer
*Attorney, Agent, or Firm*—Robert A. Harman

[57] ABSTRACT

Direct reaction of anilines with olefins occurs at elevated temperature in solution containing dissolved complex of the aniline and an eighth group metal, especially rhodium. The products are N-alkylanilines and alkylquinolines.

3 Claims, No Drawings

DIRECT REACTION OF ANILINES WITH OLEFINS

BACKGROUND OF THE INVENTION

This invention relates to production of N-alkylanilines and alkylquinolines.

It is known to produce such substituted anilines by action of alcohols on anilines. The alcohols in turn are prepared from olefins.

SUMMARY OF THE INVENTION

In accordance with our invention the subject N-alkyl anilines are produced directly in one step from anilines and olefins by heating in liquid phase such aniline, such olefin, and a dissolved complex formed between said aniline and a metal of the eighth group of the Periodic Table. It is necessary that the aniline and metal used be capable of forming a complex.

In preferred embodiments, the specific reactants are aniline and an olefin containing 2 to 12 carbon atoms, particularly ethylene, and the eighth group metal is rhodium. The temperature of such reaction mixture is suitably in the range of 100° to 200° C. Preferred reaction solvents include tetrahydrofuran, isopropanol, and benzene. The requirements for solvents are that they dissolve all of the reaction mixture ingredients, and that they be non-reactive under the reaction conditions.

EXAMPLES

The examples which follow are illustrative of the best mode which we have contemplated for carrying out our invention but are not to be interpreted as limiting the invention to details of the examples.

1. An autoclave was charged with rhodium chloride (250 mg), aniline (20 ml.) and tetrahydrofuran (20 ml.) under vacuum, and then was pressurized to about 100 atmospheres with ethylene. The reaction mixture was heated at 150° C. for about 15 hours, cooled; and analyzed. The product was approximately 20 mols of N-ethylaniline and 5 mols of quinaldine (2-methylquinoline) per mol of rhodium chloride employed in the original reaction mixture. The rhodium chloride reacts with the aniline under the specified conditions to form a complex of rhodium and aniline.

As the proportion of aniline vs. ethylene in the reaction mixture is increased, under otherwise the same reaction conditions, the proportion of N-ethylaniline vs. quinaldine increases in the reaction products.

In particular, when the liquid phase is made up from the reaction ingredients without added solvent, and the ethylene pressure is considerably lowered compared to that of Example 1, the product contains a high proportion of N-ethylaniline as shown by Example 2 which follows.

2. An autoclave was charged with rhodium chloride ($RhCl_3$-60 mg) and aniline (10 ml) under vacuum and pressurized to approximately 10 atm. with ethylene. The mixture was heated to about 100° C. for about 150 hr., cooled, and analyzed. The product was approximately 30 mols of N-ethylaniline and 2 mols quinaldine per mol of catalyst.

We claim:

1. Process of producing N-ethylaniline and quinaldine by direct reaction of aniline and ethylene, consisting essentially of heating in liquid phase in the presence or absence of a solvent selected from tetrahydrofuran, isopropanol and benzene, the reactants aniline, ethylene dissolved in the liquid phase, and a dissolved complex formed between said aniline and rhodium.

2. Process of claim 1, wherein a solvent is used selected from tetrahydrofuran, isopropanol and benzene.

3. Process of claim 1, wherein the liquid phase is made up from the reaction ingredients without added solvent.

* * * * *